United States Patent [19]

Barton

[11] Patent Number: 5,756,852

[45] Date of Patent: May 26, 1998

[54] CO-OXIDATION OF $H_2S$ AND SATURATED HYDROCARBONS

[76] Inventor: Derek H. R. Barton, Department of Chemistry, Texas A&M University, College Station, Tex. 77843-3255

[21] Appl. No.: 730,206

[22] Filed: Oct. 15, 1996

[51] Int. Cl.[6] ............................................. C07C 45/33
[52] U.S. Cl. .................... 568/360; 423/230; 423/231; 568/342; 568/385; 568/399
[58] Field of Search ........................... 568/360, 399, 568/342, 385, 390; 423/230, 231

[56] References Cited

U.S. PATENT DOCUMENTS

| | | | |
|---|---|---|---|
| 3,956,473 | 5/1976 | Mimoun et al. | 423/573 |
| 4,310,497 | 1/1982 | Deschamps et al. | 423/230 |
| 4,341,907 | 7/1982 | Zelonka | 568/360 |
| 4,900,871 | 2/1990 | Ellis et al. | 568/399 |
| 4,937,058 | 6/1990 | Dupin et al. | 423/224 |
| 5,132,472 | 7/1992 | Durante et al. | 568/399 |
| 5,208,392 | 5/1993 | Lee et al. | 568/836 |
| 5,591,419 | 1/1997 | McManus et al. | 423/230 |
| 5,603,913 | 2/1997 | Alkhayov et al. | 423/230 |

*Primary Examiner*—James H. Reamer
*Attorney, Agent, or Firm*—Pillsbury Madison & Sutro LLP

[57] ABSTRACT

Process for the catalytic oxidation of a saturated hydrocarbon to obtain a ketone which involves carrying out the oxidation simultaneously with the oxidation of $H_2S$ to form elemental sulfur and the ketone.

11 Claims, No Drawings

CO-OXIDATION OF H₂S AND SATURATED HYDROCARBONS

The present invention relates to the catalytic oxidation of saturated hydrocarbons to produce ketones.

More specifically, the invention provides a process for the synergistic co-oxidation of hydrogen sulfide and a saturated hydrocarbon to co-produce sulfur and a ketone. The invention is exemplified herein by reference to the catalytic co-oxidation of hydrogen sulfide and cyclohexane to prepare a sulfur and cyclohexanone along with cyclohexanol. However, the invention is applicable to the use of hydrocarbons generally to prepare other ketones and substituted derivatives at secondary positions.

It is well known that saturated hydrocarbons can be oxidized to form useful ketones. For example, many tons of cyclohexanone are prepared annually by the oxidation of cyclohexane for conversion into nylon. However, generally speaking, the available manufacturing processes provide only relatively low yields of the cyclohexanone. Additionally, the procedures generally used require the use of relatively high temperatures thus further complicating use of the procedures.

There is, therefore, a need for improving on available oxidation procedures for preparing ketones from hydrocarbons whereby the yield of ketone and other important secondary products can be increased. The present process provides such an improvement while at the same time enabling the use of preferred reaction conditions such as operation at ambient temperature and essentially neutral pH.

The improved process of the invention is based on the finding that by carrying out the oxidation to form ketone in combination with the H₂S oxidation a synergistic effect on the ketone formation can be obtained. At the same time, the H₂S oxidation makes possible the useful production of elemental sulfur. While H₂S from any source may be used in the process, it is particularly useful to use the H₂S in natural gas. H₂S is an undesired contaminant of natural gas and needs to be removed from the gas. The present process provides an effective way of doing this by using natural gas as the H₂S source. The H₂S can be initially removed from the gas for use in the process or the H₂S-containing natural gas can be used as such directly in the oxidation. The invention, therefore, enables two useful industrial objectives, i.e. improved ketone production by oxidation of saturated hydrocarbons, notably cyclohexanone from cyclohexane, and the use of an ecologically undesirable by-product (H₂S) to synergize the production of ketones while at the same time providing sulfur in useful elemental form.

The oxidation of H₂S to form elemental sulfur is known. It is also known to oxidize saturated hydrocarbons to make ketones using catalysts such as iron salts or complexes thereof together with oxygen and/or hydrogen peroxide (H₂O₂) as oxidizing agent. See, for example, Barton et al "The Selective Functionalization of Saturated Hydrocarbons: GIF Chemistry", Acc. Chem. Res., 1992, 25, 504–512. However, the co-oxidation of hydrogen sulfide and saturated hydrocarbons to make elemental sulfur and ketones with the consequent advantages noted herein, has not previously been disclosed.

Broadly stated, therefore, the present process involves an improvement in the catalytic oxidation of saturated hydrocarbon to form a ketone wherein the oxidation is carried out together with the oxidation of H₂S so as to form a reaction product comprising sulfur obtained from the H₂S and a ketone derived from the saturated hydrocarbon. Other substituted derivatives, particularly alcohols, are also obtained.

The invention is particularly important for use in the preparation of cyclohexanone from cyclohexane, cyclohexanol being formed as a further useful product.

As earlier noted, the co-oxidation of the hydrocarbon together with the conversion of H₂S to elemental sulfur provides several important advantages. In a preferred embodiment, an $Fe^{II}$ catalyst is used to oxidize the hydrocarbon rather than an $Fe^{III}$ catalyst because the $Fe^{II}$ form is faster than the corresponding $Fe^{III}$ form. However, during reaction, the $Fe^{II}$ tends to convert to the $Fe^{III}$ form with a consequent slowing down of the rate of oxidation. On the other hand, when the H₂S is also present, the H₂S functions to convert the $Fe^{III}$ back to the more active $Fe^{II}$ form thus synergizing the oxidation of the hydrocarbon to ketone.

While the catalyst used in the present process is preferably any $Fe^{II}$ oxidation catalyst, such as $FeCl_2$ or $Fe(ClO_4)_2$, other oxidation catalysts, e.g. copper compounds such as CuCl or like halide can also be used. The most preferred catalyst is an $Fe^{II}$ compound, e.g. $Fe(ClO_4)_2$, combined with picolinic acid or similar carboxylic acid with appropriate catalyst complexing properties, e.g. isoquinoline-1-carboxylic acid; isoquinoline-3-carboxylic acid; pyrazine-2-carboxylic acid; 4-substituted picolinic acids such as 4-lower alkyl picolinic acids; or the like. Suitable carboxylic acids, as illustrated above, are aromatic bases to which a carboxylic acid is attached in the adjacent α-position with respect to the nitrogen atom. Two of these carboxylic acids are bonded per iron atom.

The reactivity of the α-carboxylic acid can be increased by using the corresponding N-oxide, e.g. picolinic acid N-oxide. In such a case, the speed of the reaction is increased several fold. Simple carboxylic acids, e.g. acetic acid, are not suitable unless used in large excess. The complexing acid is important, because without the proper carboxylic acid, ketonization is not evident and oxygen evolution is predominant (catalase reaction).

The amount of acid complexing agent which is used can be widely varied depending on other factors, e.g. the catalyst and the nature of the complexing agent. Usually, however, from 0.5–10 mole equivalents of the acid complexing agent will be used based on the catalyst weight.

The process is preferably carried out in the presence of an inert solvent and a variety of solvents can be used for this purpose. As representative solvents, there may be mentioned solvents such as pyridine, acetonitrile, acetone and ethyl acetate. In some cases, e.g. when using cyclohexane, the reaction can also be run without solvent. However, unless pyridine is used as the solvent, it is essential to include a pyridine type base in an amount sufficient to complex with the catalyst. Such complexing is essential for optimum results. The amount of complexing base can be widely varied but will usually fall in the range of 1–10 mole equivalents of the catalyst. Suitable pyridine type bases are pyridine itself, 3- and 4-methylpyridines and 4-t-butylpyridine. The latter has a higher boiling point which aids the separation of cyclohexanol and cyclohexanone. Quinoline and isoquinoline as well as their simple alkyl derivatives can also be used. Bases like 2,6-di-t-butyl-4-methylpyridine, with a hindered nitrogen cannot be used since they do not complex to iron.

The oxidation is desirably carried out using both hydrogen peroxide and oxygen. The oxygen may be pure oxygen or in the form of air. It is also possible to effectively operate the process using only hydrogen peroxide or only oxygen although optimum results appear to be obtained using the combination of hydrogen peroxide and oxygen (air). Other peroxides, e.g. t-butylhydroperoxide or cumyl hydroperoxide may also be used in lieu of, or in addition to, hydrogen peroxide.

The process is of particular utility in the preparation of cyclohexanone from cyclohexane. However, the process may also be used to prepare other ketones, both cyclic and non-cyclic, using the appropriate saturated hydrocarbon starting material, e.g. $C_3$–$C_{20}$, preferably $C_3$–$C_{12}$, alkanes or cycloalkanes other than cyclohexane such as cyclopentane, cyclooctane and cyclododecane.

Any convenient source of $H_2S$ can be used in the present process. As earlier noted, one supply is natural gas which contains $H_2S$. The $H_2S$ may be separated from the natural gas before use in the process or the contaminated natural gas may itself be used directly as the reactant.

The process is preferably carried out at essentially atmospheric pressure and ambient or room temperature (20°–25° C.) although if desired, elevated temperatures and pressures may be used provided the conditions are such that the hydrocarbon starting material and solvent are in the liquid phase. A particular advantage of the process, however, is that it is effectively operated at room temperature. This is in contrast to the autoxidation processes which are generally used for making cyclohexanone and require the use of relatively high temperatures. The yields obtainable with the present process are also markedly higher than those obtained with the autoxidation process.

The process also is operated at essentially neutral pH although slightly acidic or basic conditions can be used, if desired.

A preferred way of carrying out the present process is as follows:

Cyclohexane and an $Fe^{II}$ or $Fe^{III}$ catalyst in pyridine, or acetonitrile to which pyridine or an alkyl pyridine base has been added, are placed in a flask or other suitable reaction vessel at room temperature. The $Fe^{II}$ or $Fe^{III}$ catalyst advantageously consists of $FeCl_2$, Fe $(ClO_4)_2$ or $FeCl_3$ to which picolinic acid or other suitable complexing acid has been added. When an $Fe^{III}$ catalyst is used, this is reduced in situ to the $Fe^{II}$ form.

A stream of oxygen or air is passed through the solution. A slow stream of $H_2S$ is also passed through the solution at a concentration sufficient to keep essentially all of the iron in the $Fe^{II}$ state. At the same time, hydrogen peroxide (e.g. 30% by weight solution) is added at a convenient rate and in amount sufficient to conduct the oxidation.

Without intending to be limited to any particular theory of operation, it appears that the reactions involved can be illustrated as follows:

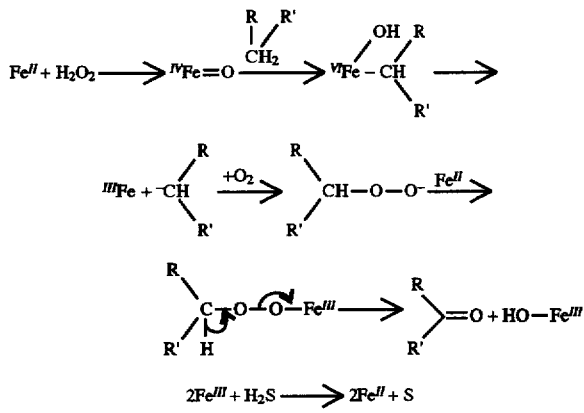

Results of such oxidation indicate that up to about 1.5 times the theoretical amount of ketone can be obtained from the foregoing reaction. This suggests that some triplet oxygen has reacted with the $Fe^{II}$ to give $Fe^{III}$ and superoxide and that the latter has participated directly or indirectly in the reaction.

It will be understood that the R and $R^1$ substituents shown above can be separate saturated hydrocarbon groups, e.g. alkyl of 1–12 carbon atoms or they may be combined to provide a single methylene group as necessary to complete a cyclic ring of, for example, 3–12 ring carbons such as in cyclohexane.

In a modification of the above procedure, the $Fe^{II}$ catalyst can be supplemented or replaced by, for example, a copper salt such as $CuCl_2$ or the equivalent cobalt salt.

A straightforward work-up procedure may be used to recover the desired products which, in the case where cyclohexane is used as the starting hydrocarbon, will consist essentially of sulfur, cyclohexanone and cyclohexanol. Work-up is usually begun when the reaction mixture reaches a 20–30% ketone concentration. At this point, the reaction may be terminated by discontinuing the addition of $H_2O_2$, oxygen and $H_2S$. The solution is then filtered to remove precipitated sulfur followed by distillation of the filtrate. Cyclohexane starting material and acetonitrile solvent distill off at 80° C. and are recovered. The pressure on the remaining solution is then lowered to below atmospheric pressure and the solution distilled at about the same temperature as before (about 80° C.) to recover the cyclohexanone. The cyclohexane-acetonitrile mixture recovered by initial distillation can be recycled for further reaction, with added cyclohexane, to prepare additional ketone and sulfur.

The invention is illustrated by, but not limited to, the following examples:

EXAMPLE 1

$Fe(ClO_4)_2 \cdot 4H_2O$ (0.363 g, 1 mmol), picolinic acid (0.369 g, 3 mmol) and cyclohexane (3.366 g, 40 mmol) were dissolved in 33 ml of pyridine. The solution was cooled to 0° C. A slow stream of $H_2S$ (g) was then continuously bubbled through the reaction mixture. Anhydrous $H_2O_2$(4×1 mmol) in pyridine (4×2 ml) was then added in four portions at 20 minute intervals. Upon each addition of the $H_2O_2$ solution, a stream of $O_2$ was bubbled through the reaction mixture for 10 minutes. The products of the reaction were analyzed by gas chromatography with naphthalene being used as an internal standard. Yield: cyclohexanone (1.65 mmol), cyclohexanol (0.47 mmol), unidentified products (0.25 mmol). Efficiency=94%.

EXAMPLE 2

$Fe(ClO_4)_2 \cdot 4H_2O$ (0.363 g, 1 mmol), picolinic acid (0.369 g, 3 mmol) and 4-t-butylpyridine (2 ml, 13.5 mmol) and cyclohexane (1.683 g, 20 mmol) were dissolved in 31 ml of acetonitrile. The reaction mixture was stirred at room temperature under a slow stream of $O_2$, $H_2O_2$(0.3 ml, 3 mmol) and $H_2S$ (g) (5–6 mmol) were added simultaneously to the reaction mixture, portionwise over 2h. The reaction mixture was stirred for a further 1h. The products of the reaction were analyzed by gas chromatography with naphthalene being used as an internal standard. Yield: cyclohexanone (3.11 mmol), cyclohexanol (0.58 mmol).

EXAMPLE 3

$Fe(ClO_4)_2 \cdot 4H_2O$ (0.363 g, 1 mmol), picolinic acid (0.369 g, 3 mmol), 4-t-butylpyridine (2 ml, 13.5 mmol and cyclohexane (1.683 g, 20 mmol) were dissolved in 31 ml of acetonitrile. The reaction mixture was stirred at room temperature under a slow stream of $O_2$, $H_2S$ (g) (15–20 mmol)

was then added portionwise over 3.5 h. The products of the reaction were analyzed by gas chromatography with naphthalene being used as an internal standard. Yield: cyclohexanone (1.15 mmol), cyclohexanol (1.63 mmol).

EXAMPLE 4

Example 3 was repeated except that CuCl (2.5 mmol) was substituted for Fe(ClO$_4$)$_2$ and the amount of picolinic acid was increased to 6 mmol. The yields obtained were cyclohexanone (2.21 mmol) and cyclohexanol (2.86 mmol).

EXAMPLE 5

Example 3 was repeated on a larger scale as follows:

FeCl$_2$.4H$_2$O (3.96 g, 20 mmol), picolinic acid (7.39 g, 60 mmol) and 4-tert-butylpyridine (23 mL, 21 g) were dissolved in 80 mL of acetonitrile (62 g) and 85 mL of cyclohexane (66 g, 784 mmol) was added to the mixture. The mixture was stirred in a cold water bath under a slow stream of oxygen. The reaction was initiated by bubbling hydrogen sulfide gas portionwise through the mixture. The reaction was monitored by gas chromatography. After 36 h, the precipitated sulfur was filtered off and washed with 80 g of acetonitrile. The combined filtrates were distilled to recover cyclohexane and acetonitrile. The results obtained are summarized in the following table:

| Entry | Time (h) | Cyclohexanone (mmol) | Cyclohexanol (mmol) | Total (mmol) | Conversion (%) |
|---|---|---|---|---|---|
| 1 | 4 | 15.97 | 4.91 | 20.88 | 2.66 |
| 2 | 8 | 22.43 | 8.39 | 30.82 | 3.93 |
| 3 | 12 | 31.57 | 10.30 | 41.87 | 5.34 |
| 4 | 16 | 34.90 | 12.05 | 46.95 | 5.99 |
| 5 | 20 | 43.08 | 17.00 | 60.08 | 7.66 |
| 6 | 24 | 47.66 | 18.91 | 66.57 | 8.49 |
| 7 | 28 | 55.32 | 22.06 | 77.38 | 9.87 |
| 8 | 36 | 78.97 | 33.35 | 112.32 | 14.33 |

Mass Balance

Amount of solvent (cyclohexane and acetonitrile) recovered: 178 g (85% of the theoretical amount)

Amount of oxidized hydrocarbon (cyclohexanone and cyclohexanol) obtained: 9.2 g (83% of the theoretical amount)

Amount of sulfur recovered: 21 g (ca. 625 mmol)

As will be seen from the foregoing, the invention provides an effective way of catalytically oxidizing saturated hydrocarbons selectively and quantitatively into ketones and other useful derivatives, notably alcohols. The use of H$_2$S in the co-oxidation functions to improve catalytic activity, particularly when Fe$^{II}$ is used. At the same time, the process enables the removal and/or use of H$_2$S present as an unwanted constituent of natural gas or the like. The process thus enables the use of an ecologically undesirable by-product to indirectly oxidize saturated hydrocarbons to valuable and useful chemical products. It is particularly useful that the process can be carried out at room temperature and at or near neutral pH.

As a further modification of the invention, it is noted that by carrying out the process using H$_2$O$_2$ as described except in the absence of oxygen and in the presence of excess chloride, bromide, azide, thiocyanate and nitrite anions, it is possible to also obtain good to excellent yields of the appropriate secondary substituted derivative of the saturated hydrocarbon. Thus, cyclohexane affords cyclohexyl chloride, bromide, azide, thiocyanate and nitro derivatives in a preparatively useful manner.

Various other modifications may be made in the invention without departing from the scope and spirit thereof as defined in the following claims wherein:

What is claimed is:

1. In a process for the catalytic oxidation of a saturated hydrocarbon to produce a ketone, the improvement which comprises carrying out said oxidation simultaneously with the oxidation of hydrogen sulfide to form elemental sulfur together with the ketone, said co-oxidation of saturated hydrocarbon and hydrogen sulfide being carried out in the presence of an iron or copper oxidation catalyst complexed with pyridine or pyridine-type complexing base and a complexing aromatic carboxylic acid whereby a synergistic increase in the ketone formation is obtained along with the production of the elemental sulfur.

2. The process of claim 1 wherein the hydrocarbon is cyclohexane and the ketone is cyclohexanone.

3. The process of claim 1 wherein the oxidation is carried out in the presence of a solvent.

4. The process of claim 3 wherein the oxidation is carried out in the presence of an Fe$^{II}$ catalyst or Fe$^{III}$ catalyst which is reduced in situ to an Fe$^{II}$ catalyst.

5. The process of claim 3 wherein the solvent is pyridine or acetonitrile.

6. The process of claim 3 wherein the solvent includes a pyridine type base which comprises a base for complexing with the Fe$^{II}$ compound.

7. The process of claim 1 which is carried out at room temperature and essentially neutral pH.

8. The process of claim 1 wherein the oxidation is carried out using at least one member of the group consisting of hydrogen peroxide and oxygen or air.

9. The process of claim 8 wherein the hydrocarbon is cyclohexane, the catalyst is Fe(ClO$_4$)$_2$ and the oxidation is carried out at room temperature and essentially neutral pH.

10. The process of claim 1 wherein the hydrogen sulfide is obtained from natural gas containing the sulfide as contaminant.

11. The process of claim 1 wherein the catalyst is an Fe$^{II}$ oxidation catalyst complexed with pyridine or alkyl pyridine and a complexing carboxylic acid selected from the group consisting of picolinic acid, isoquinoline carboxylic acid or pyrazine carboxylic acid and the oxidation is carried out at atmospheric pressure and temperature and essentially neutral pH.

* * * * *